US009636049B2

(12) United States Patent
Roesicke et al.

(10) Patent No.: US 9,636,049 B2
(45) Date of Patent: May 2, 2017

(54) METHOD OF COMPRESSION DATA FROM IN-VIVO MEASUREMENTS OF AN ANALYTE CONCENTRATION IN A HUMAN

(71) Applicants: ROCHE DIAGNOSTICS OPERATIONS, INC., Indianapolis, IN (US); Ulrich Schwind, Schifferstadt (DE)

(72) Inventors: Bernd Roesicke, Mannheim (DE); Karin Obermaier, Bruehl (DE); Stefan Lindegger, Lotzwil (CH); Andreas Menke, Mannheim (DE); Joerg Scherer, Zuchwil (CH); Karin Schwind, Schifferstadt (DE); Otto Gaa, Worms (DE); Gregor Bainczyk, Mannheim (DE); Michael Marquant, Mannheim (DE); Sandro Niederhauser, Rutschelen (CH); Michael Schoemaker, Mannheim (DE); Martin Mueri, Basel (CH)

(73) Assignee: ROCHE DIAGNOSTICS OPERATIONS, INC., Indianapolis, IN (US)

(*) Notice: Subject to any disclaimer, the term of this patent is extended or adjusted under 35 U.S.C. 154(b) by 515 days.

(21) Appl. No.: 14/076,428

(22) Filed: Nov. 11, 2013

(65) Prior Publication Data

US 2014/0066730 A1 Mar. 6, 2014

Related U.S. Application Data

(63) Continuation of application No. 12/052,382, filed on Mar. 20, 2008, now Pat. No. 8,721,544.

(30) Foreign Application Priority Data

Mar. 20, 2007 (EP) .................................... 07005638
Dec. 13, 2007 (EP) .................................... 07024174

(51) Int. Cl.
*A61B 5/00* (2006.01)
*A61B 5/145* (2006.01)
*A61B 5/1486* (2006.01)

(52) U.S. Cl.
CPC ...... *A61B 5/14503* (2013.01); *A61B 5/14532* (2013.01); *A61B 5/14546* (2013.01);
(Continued)

(58) Field of Classification Search
USPC .................... 600/365, 309, 345, 347; 703/11
See application file for complete search history.

(56) References Cited

U.S. PATENT DOCUMENTS 5,235,510 A    8/1993  Yamada et al.
5,748,781 A *  5/1998  Datta ...................... G06T 9/004
                                                                 345/673

(Continued)

FOREIGN PATENT DOCUMENTS

EP     0789540 B1    9/2001
EP     1382363 A1    1/2004

(Continued)

OTHER PUBLICATIONS

Lo et al, International Workshop on Body Sensors, 2005, pp. 1-5 (Lo).*

(Continued)

*Primary Examiner* — Michael Kahelin
*Assistant Examiner* — Mitchell E Alter
(74) *Attorney, Agent, or Firm* — Faegre Baker Daniels LLP (57) ABSTRACT

The analyte concentration, such as glucose, in a human or animal body is measured with an implantable sensor that generates measurement signals. The measurement signals are compressed through statistical techniques to produced compressed measurement data that can is easier to process (Continued)

and communicate. A base station carries the implantable sensor along with a signal processor, memory, and a transmitter. A display device is also disclosed that can receive the compressed measurement data from the base station for further processing and display.

15 Claims, 6 Drawing Sheets

(52) U.S. Cl.
CPC ........ *A61B 5/14865* (2013.01); *A61B 5/6849* (2013.01); *A61B 5/0002* (2013.01); *A61B 5/7232* (2013.01)

(56) References Cited

U.S. PATENT DOCUMENTS

| | | | |
|---|---|---|---|
| 5,800,420 A | 9/1998 | Gross et al. | |
| 5,820,622 A | 10/1998 | Gross et al. | |
| 5,997,501 A | 12/1999 | Gross et al. | |
| 6,275,717 B1 | 8/2001 | Gross et al. | |
| 6,315,738 B1 | 11/2001 | Nishikawa et al. | |
| 6,360,888 B1 | 3/2002 | McIvor et al. | |
| 6,418,332 B1 | 7/2002 | Mastrotaro et al. | |
| 6,520,326 B2 | 2/2003 | McIvor et al. | |
| 6,579,690 B1 | 6/2003 | Bonnecaze et al. | |
| 6,584,335 B1 | 6/2003 | Hear et al. | |
| 6,589,229 B1 | 7/2003 | Connelly et al. | |
| 6,740,059 B2 | 5/2004 | Flaherty | |
| 6,749,587 B2 | 6/2004 | Flaherty | |
| 6,837,988 B2 | 1/2005 | Leong et al. | |
| 6,920,345 B2 | 7/2005 | Al-Ali et al. | |
| 7,024,236 B2 | 4/2006 | Ford et al. | |
| 7,029,455 B2 | 4/2006 | Flaherty | |
| 7,052,483 B2 | 5/2006 | Wojcik | |
| 7,220,241 B2 | 5/2007 | Csincsura et al. | |
| 7,768,386 B2 * | 8/2010 | Hayter | G06F 19/3412 340/3.1 |
| 2002/0002326 A1 | 1/2002 | Causey, III et al. | |
| 2002/0029058 A1 | 3/2002 | Levaughn et al. | |
| 2002/0032384 A1* | 3/2002 | Raymond | A61B 5/02055 600/513 |
| 2002/0040208 A1 | 4/2002 | Flaherty et al. | |
| 2002/0072733 A1 | 6/2002 | Flaherty | |
| 2002/0169439 A1 | 11/2002 | Flaherty | |
| 2002/0185384 A1 | 12/2002 | Leong et al. | |
| 2003/0050573 A1 | 3/2003 | Kuhr et al. | |
| 2003/0097092 A1 | 5/2003 | Flaherty | |
| 2004/0087894 A1 | 5/2004 | Flaherty | |
| 2004/0133164 A1 | 7/2004 | Funderburk et al. | |
| 2004/0147822 A1 | 7/2004 | Al-Ali et al. | |
| 2004/0204673 A1 | 10/2004 | Flaherty | |
| 2004/0217018 A1 | 11/2004 | Leong et al. | |
| 2004/0230233 A1 | 11/2004 | Gunderson et al. | |
| 2004/0249254 A1 | 12/2004 | Racchini et al. | |
| 2004/0260233 A1 | 12/2004 | Garibotto et al. | |
| 2004/0263354 A1 | 12/2004 | Mann et al. | |
| 2005/0021066 A1 | 1/2005 | Kuhr et al. | |
| 2005/0143635 A1 | 6/2005 | Kamath et al. | |
| 2005/0154271 A1 | 7/2005 | Rasdal et al. | |
| 2005/0171512 A1 | 8/2005 | Flaherty | |
| 2006/0030815 A1 | 2/2006 | Csincsura et al. | |
| 2006/0183984 A1 | 8/2006 | Dobbles et al. | |
| 2006/0183987 A1 | 8/2006 | Murray | |
| 2006/0258929 A1 | 11/2006 | Goode, Jr. et al. | |
| 2007/0078323 A1 | 4/2007 | Reggiardo et al. | |
| 2007/0265515 A1 | 11/2007 | Brister et al. | |

FOREIGN PATENT DOCUMENTS

| | | |
|---|---|---|
| EP | 1177802 B1 | 9/2004 |
| EP | 1466558 A2 | 10/2004 |
| EP | 1266608 B1 | 8/2006 |
| EP | 1618908 B1 | 11/2006 |
| EP | 1335764 B1 | 6/2007 |
| WO | 98/58250 A2 | 12/1998 |
| WO | 01/00085 | 1/2001 |
| WO | 02/20073 A2 | 3/2002 |
| WO | 02/28454 A2 | 4/2002 |
| WO | 02/068015 A2 | 9/2002 |
| WO | 2004/088275 A2 | 10/2004 |
| WO | 2005/052543 A2 | 6/2005 |
| WO | 2005/057168 A2 | 6/2005 |
| WO | 2005/057173 A2 | 6/2005 |
| WO | 2005/057175 A2 | 6/2005 |
| WO | 2005/063115 A1 | 7/2005 |
| WO | 2005/076391 A1 | 8/2005 |
| WO | 2006/001024 A2 | 1/2006 |
| WO | 2006/017358 A1 | 2/2006 |
| WO | 2006/017359 A1 | 2/2006 |
| WO | 2006/075016 A1 | 7/2006 |
| WO | 2006/108809 A1 | 10/2006 |
| WO | 2006/114297 | 11/2006 |

OTHER PUBLICATIONS

Bernholt, T., et al. "Modified repeated median filters" Statistics and Computing, Jun. 2006, vol. 16, Issue 2, pp. 177-192 (Bernholt).*
Fried et al. (Computational Statistics and Data Analysis, 2006, vol. 50, pp. 2313-2338).
Lo et al. (International Workshop on Body Sensors, 2005, pp. 1-5).
Roland Fired, et al., Repeated median and hybrid filters, Preprint Submitted to Computational Statistics & Data Analysis, Aug. 4, 2004, Printed from internet (htt;://ls2-www.cs.uni-dortmund.de/~bernholt/ps/Repeated_Median_and_Hybrid_Filters.pdf), pp. 1-29.

* cited by examiner

METHOD OF COMPRESSION DATA FROM IN-VIVO MEASUREMENTS OF AN ANALYTE CONCENTRATION IN A HUMAN

CROSS REFERENCE TO RELATED APPLICATION

This application claims priority to and is a continuation of U.S. patent application Ser. No. 12/052,382, filed Mar. 20, 2008, which claims priority to European Patent Application No. EP 07 005 638.7 filed Mar. 20, 2007 and European Patent Application No. EP 07 024 174.0 filed Dec. 13, 2007, the disclosures of which are hereby expressly incorporated by reference herein in their entirety.

BACKGROUND

1. Field of the Disclosure

This disclosure relates to a system for in-vitro measurement of an analyte concentration in a human or animal body.

2. Description of the Related Art

Systems of this type for in-vivo measurement of analyte concentrations usually comprise replaceable sensors as replaceable or consumable components and a long-lived base station to which the replaceable sensors are connected. An example of such system is disclosed in US 2004/0133164 A1.

In-vitro measurement system can be monitor analyte concentration over many hours or days generate large amounts of data that can be difficult to store and transmit.

SUMMARY

The measure according to embodiments the invention to have the analytical unit of the base station, in operation, subject to statistical analysis the measuring signals that are supplied as raw data by a sensor connected to it and generate from the raw data condensed measuring data for transmission by the transmitter to the display device, and to have the display device contain an electronic analytical unit, which, in operation, determines an analyte concentration value by analyzing the condensed measuring data, allows the volume of data to be transmitted and therefore the energy consumption to be kept advantageously low while the advantage of a high measuring rate can still be utilized.

In order to keep the weight of the system components that are carried on the body as low as possible, it is advantageous for the energy consumption of the base station to be as low as possible, since a smaller and lighter-weight battery is then sufficient for supplying this system component with energy for a sufficiently long period of time.

Preferably, measuring or sensor signals that are supplied by a sensor are recorded for first time intervals, for example of duration from 0.5 seconds to 5 seconds, as raw data. The raw data are then used to generate condensed measuring data for second time intervals, for example of 10 to 1,000 seconds, whereby the second time intervals are at least 10-fold, preferably at least 50-fold, longer than the first time intervals. Preferably, both the first time intervals and the second time intervals each are invariable.

Accordingly, exactly one measuring signal value that is correlated to the analyte concentration to be determined is stored in the base station for a first time interval. In order to reduce the energy consumption associated with the transmission of data, it is preferred to generate from each at least 10, in particular at least 50, signal values that are stored as raw data a condensed measuring data value for a correspondingly larger time interval.

Measuring signals can be generated in very short time intervals of, for example, one second through the use of implantable sensors such that very large volumes of raw data may be obtained upon sustained measuring. Another aspect of embodiment of the invention, which may be of significance independently, relates to a method for condensing raw data that were determined using an implanted sensor, in which method pairs of measuring signal values are formed from the raw data generated for a time interval, then a slope of a line connecting the two values of a pair of values is determined for each pair of measuring signal values, then a median value of the slopes thus determined is calculated, and then a condensed data value is calculated for said time interval from the median value of the slope and the condensed data value of the preceding time interval.

Since, initially, no condensed data value is available for the first time interval, the median or, for example, the arithmetic mean of the raw data values determined for the first time interval may be used as condensed data value of the first time interval. Raw data values that are non-plausible, for example due to uncommonly strong deviation from the remaining raw data values of a time interval, can be disregarded in the determination of the condensed data value, for example in that they are not used for forming pairs of values.

Preferably, the measuring signals supplied by a sensor are condensed as raw data in the base station into measuring data in a first step of analysis, the condensed measuring data are transmitted to the display device, and analyte concentration values are calculated from the measuring data by means of the analytical unit of the display device in a further step of analysis. Having a two-step analysis of this type including a first step of analysis in the base station and a further step of analysis in the display device allows the advantages of continuous or quasi-continuous measurement with regard to currentness and accuracy to be utilized and still keep the data volumes to be transmitted by the base station small. In particular, relatively simple and therefore cost-efficient microprocessors in the base station are sufficient for condensing the raw data, for example by forming the mean or by application of the repeated median procedure. For final analysis of the condensed measuring data, a powerful and more expensive microprocessor can be used in the display device, and can be used therein for other tasks as well, for example for a graphic presentation of the analyte concentration values thus determined and linking to other data that have been generated and stored by the display device or originate from other sources. Therefore, another aspect of the invention that may also be of significance independently relates to a system for in-vivo measurement of an analyte concentration in a human or animal body having at least one implantable sensor for generating measuring signals that are correlated to the analyte concentration to be measured, a base station that can be connected to the sensor and contains an electronic analytical unit for analysis of measuring signals of a sensor connected to it, and a transmitter for wireless transmission of analytical results, and a display device that comprises a receiver for receiving the analytical signals transmitted by the base station and a display facility for displaying analyte concentration values, whereby the analytical unit of the base station, in operation, subjects the raw data supplied by a sensor connected to it to statistical analysis and generates from the raw data condensed measuring data that are then transmitted by the transmitter to the display device, and the display device contains an electronic analytical unit that, in operation, determines an analyte concentration value by analysis of the measuring data.

Therefore, a further aspect of embodiments of the invention that may be of significance independently relates to a system for in-vivo measurement of an analyte concentration in a human or animal body having at least one implantable sensor for generating measuring signals that are correlated to the analyte concentration to be measured, a base station that can be coupled to the sensor and contains a potentiostat for supplying voltage to a sensor of this type, as well as a receiver and a transmitter for wireless transmission of data, whereby the base station is adapted such that the transmission of data is initiated by receiving a control signal that is transmitted by wireless means. In order to prevent miscommunication with devices that are not part of the system, the control signal can include a characteristic identifier that is used by the sampling device to identify itself with respect to the base station. Likewise, the base station can transmit a characteristic identifier signal when it communicates in order to identify itself.

The data can, in particular, be condensed measuring data that have been determined by an analytical unit that is contained in the base station from raw data that was obtained as measuring signals of a connected sensor. A control signal initiating transmission of the measuring data can, for example, be transmitted by a display device.

In systems for in-vivo measurement of analyte concentrations, for example glucose, sensors usually need to be replaced every few days. Replacing a sensor and correctly connecting a new sensor to the base station prove to be cumbersome for many users, in particular for patients whose manual dexterity is restricted due to age or disease. By having the sensor be part of a replaceable sensor carrier unit that comprises a sealed housing in which the sensor is disposed, and having the housing of the sensor carrier unit lock to the base station in order to couple the sensor to the base station, the handling of the system, in particular the replacing of sensors, can be simplified significantly such that a system according to the invention can, in particular, be used by medical laymen also.

The scaled housing of the sensor carrier unit protects the sensitive sensor from adverse environmental influences. For this reason, the sensor carrier unit can be handled by laymen also without a risk of damaging or contaminating the sensor. Coupling the sensor carrier unit to the base station is made easy by locking. The sensor can be exposed for insertion after coupling, for example by means of a predetermined breaking point for the sensor that is provided on the housing of the sensor carrier unit.

The sensor can be coupled electrically to the base station by means of a data line, for example in the case of electrochemical sensors being used. If optical sensors are used, such as those known from U.S. Pat. No. 6,584,335, the sensor can just as well be coupled to the base station by means of an optical data line.

However, it is also feasible for the sensor carrier unit to communicate with the base station in a wireless fashion, for example inductive or by means of RF1D. Having wireless communication between sensor carrier unit and base station is advantageous in that sealing problems of the sensor carrier unit and base station, which are carried on the body by the patient, are largely prevented. In particular, the risk of leakage current interfering with measuring results can also be reduced. A wireless communication between the sensor carrier unit and the base station locked to it, i.e. over a very short distance, can be implemented in a cost-efficient fashion, for example by means of inductive coupling. A relatively cost-intensive transmitter with a larger range of, for example, one meter for communication with the display device is only needed in the base station.

The sensor carrier unit preferably contains a data carrier bearing calibration data of the sensor. This measure is advantageous in that it ensures reliably that data determined by a sensor are always analyzed using matching calibration data. In particular in the case of a sensor carrier unit that communicates with the base station in a wireless fashion, it can be advantageous to dispose in the housing of the sensor carrier unit a data carrier onto which calibration data can be written through the sealed housing of the sensor carrier unit, for example an electronic memory that can also be read and/or written to by means of RFID. By this means it is feasible to sterilize the entire sensor carrier unit by exposure to radiation, determine the needed calibration data after the sterilization process using random samples of a production hatch, and then write the calibration data onto the data carriers of the sensor carrier units. It is also feasible, though, to dispose the sensor in a first chamber and the data carrier in a second chamber of the sensor carrier unit. By this means, the sensor can be sterilized inside a sealed chamber and a data carrier bearing calibration data can be inserted in the second chamber subsequently.

The sensor carrier unit preferably contains a battery. This battery can, in particular, also be used for supplying power to the base station such that consumable components of the system according to the invention can advantageously be combined in the sensor carrier unit. It is particularly preferred for the battery to be surrounded by the housing of the sensor carrier unit. This measure is advantageous in that the battery is well-protected and manipulations by users are made more difficult.

In a system according to the invention, the base station preferably comprises a housing that is adjusted to match the sensor carrier unit and comprises an interface that matches the interface of the sensor carrier unit such that the sensor becomes electrically connected to the base station by placing the housing of the base station against the housing of the sensor carrier unit. A reversible, i.e. subsequently releasable, coupling of the sensor carrier unit to the base station can be implemented, for example, by means of a form-fitting or a non-positive connection. In this context, it is particularly advantageous and therefore preferred for the sensor carrier unit to lock to the base station since this can be perceived by a user such that it is thus signaled to him that the sensor carrier unit is correctly connected to the base station.

The sensor can, for example, be an amperometric sensor that is supplied with power by a potentiostat that is contained in the base station. However, electrochemical sensors needing no potentiostat can be used for the system just as well, for example coulomb-metric sensors or, for example, optical sensors.

BRIEF DESCRIPTION OF THE DRAWINGS

Further details of embodiments of the invention are illustrated by means of exemplary embodiments and reference being made to the appended drawings.

DETAILED DESCRIPTION

Figure 1:
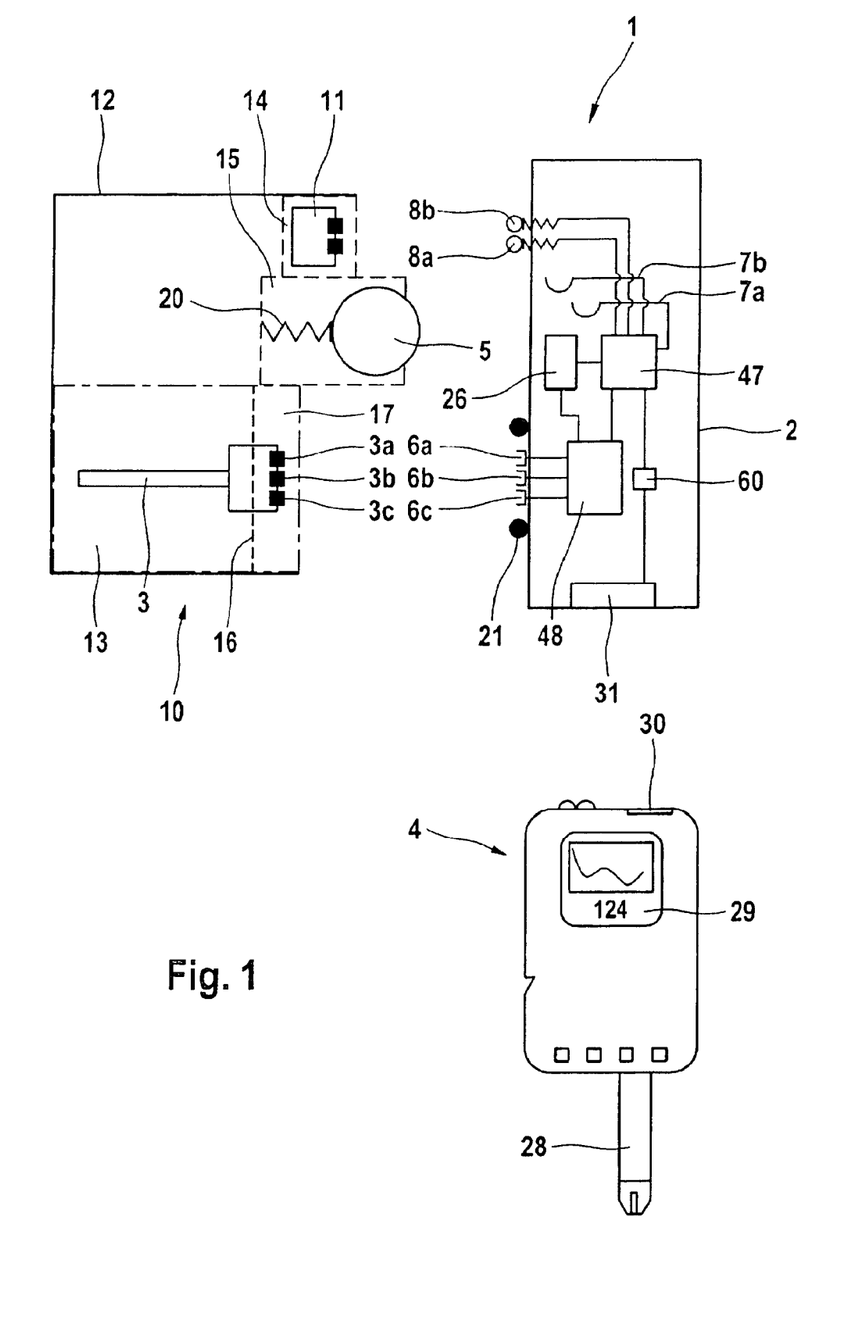
FIG. 1 shows a schematic view of an exemplary embodiment of a system according to the invention for in-vivo measurement of an analyte concentration in a human or animal body.
Figure 3:
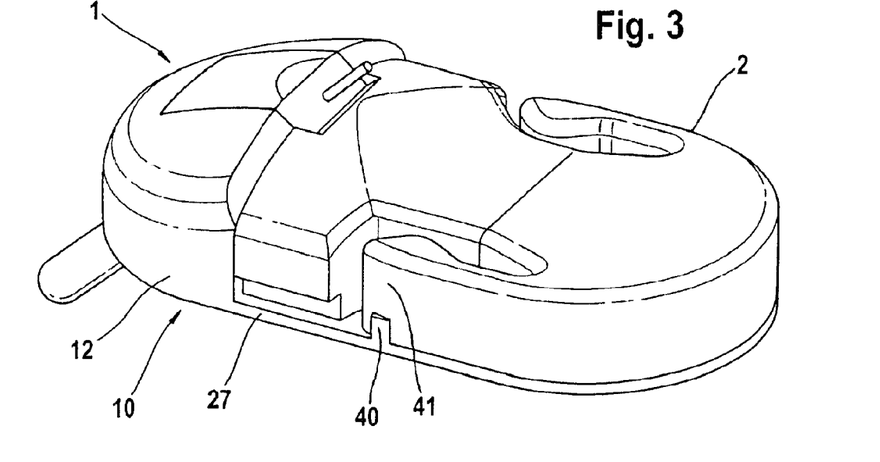
FIG. 3 shows an exemplary embodiment of a base station and a sensor carrier unit of a system according to FIG. 1 connected to it.

FIG. 1 shows a schematic view of a system 1 for in-vivo measurement of an analyte concentration in a human or animal body. The system I includes, as consumable or replaceable component, a sensor carrier unit 10 having at least one implantable sensor 3 for generating measuring signals that are correlated to the analyte concentration to be measured. The sensor carrier unit 10 has a housing 12 that is shown in FIG. 3 to have a bottom 27 that extends along the body surface when the sensor carrier unit 10 is attached to the body of a patient according to its purpose. The sensor carrier unit 10 contains a battery 5 and a data carrier 11 bearing calibration data of the sensor 3. The battery 5 and the data carrier 11 are disposed within the housing 12 of the sensor carrier unit 10 such as to be inaccessible to a user in order to exclude, to the extent possible, erroneous results or damage from inappropriate handling.

The sensor carrier unit 10 can be connected to a base station 2 by means of a catch mechanism. The base station 2 is a multiply usable component of the system 1. A spent sensor carrier unit 1 0 can be uncoupled from the base station 2 and replaced by a new sensor carrier unit 10. The base station 2 contains a potentiostat 48 for supplying voltage to a sensor 3 of a sensor carrier unit 10 connected thereto, an electronic analytical unit 47 for analysis of measuring signals of a sensor 3 connected thereto, and a communication unit 31 having a transmitter for wireless transmission of analytical results. The base station 2 further contains an electronic intermediary memory 60 for storing measuring values or data obtained therefrom. In the exemplary embodiment shown, the base station 2 contains a memory for intermediate storage of raw data, for example a RAM memory, and a memory for storing condensed measuring data, for example an EEPROM or flash memory, until such data is transmitted and/or for the storage of data that were passed on to the base station 2 by the display device 4.

The sensor carrier unit 10 has a housing 12 having an interface for electric connection of the sensor 3 to the base station 2. In corresponding fashion, the base station 2 has a housing that is adapted to match the sensor carrier unit 10 and comprises an interface that matches the interface of the sensor carrier unit 10 such that the sensor 3 can be connected electrically to the potentiostat 48 by placing the housing of the base station 2 against the housing 12 of the sensor carrier unit 10 such that sensor contacts 3a, 3b, and 3c are connected to connections 6a, 6b, and 6c of the base station. In the process, the battery 5 and the data carrier 11 are also connected to contacts 7a, 7b and 8a, 8b, respectively, of the interface of the base station 2. The mutually matching interfaces of the sensor carrier unit 10 and base station 2 can form a plug-in connection whereby the male part of the plug-in connection can be disposed on the base station 2 and the female part on the sensor carrier unit 10 or vice versa.

A start-up is caused by connecting the sensor carrier unit 10 to the base station 2, in particular the measuring process of sensor 3 is initiated in this way. Accordingly, the sensor 3 is activated by coupling to the base station 2 such that it commences to supply measuring signals. A reset and initialization command for this purpose can be effected in a processor forming the analytical unit 47 upon connecting the sensor carrier unit 10 to the base station 2. This measure is advantageous in that no switch is required to switch-on the system and the start-up of the system is effected by a defined action of the user, namely by connecting a sensor carrier unit 10 to the base station 2. As soon as a voltage is applied by connecting the battery to the potentiostat 48, charge carriers are automatically transported away from the working electrode such that the risk of charge accumulation is minimized.

A further long-lived component belonging to the system is a display unit 4 that comprises a receiver 30 for receiving the data transmitted by the base station 2, and a display facility 29, for example a liquid crystal display, for displaying analyte concentration values. The receiver 30 of the display device 4 preferably also contains a transmitter and the transmitter 31 of the base station also contains a receiver such that a bidirectional communication between base station 2 and display device 4 is feasible. Transmissions of the base station 2 and of the display device 4 can be characterized by means of an identifier, for example a bit sequence. In order to exclude miscommunication with devices of other patients, signals that do not bear the expected identifier may be ignored by the base station 2 and the display device 4.

The distribution of functions and components to the system components, sensor carrier unit 10, base station 2, and display device 4, as described, allows an optimal result to be attained with regard to the weight of the system components that are to be carried on the body, the costs, and the user convenience. Consumable components of the system, for example sensor 3 and battery 5, are part of the sensor carrier unit 10 that needs to be replaced periodically, for example every 5 days, such that all consumable components can be replaced as easily as possible. In order to generate measuring data using a sensor 3 of the sensor carrier unit 10, aside from the consumable components, long-lived system components, such as for example the potentiostat 48 and an analytical unit, are also required. The distribution of these long-lived system components to the base station 2, which is also carried on the body, and the display device 4 was effected to provide the best-possible user convenience in order to be able to implement the base station 2 to be as small and lightweight as possible. For this reason, the base station 2 contains a potentiostat 48 for supplying a sensor 3 connected to it, a transmitter for transmitting data to the display device 4, and an analytical unit 48 for preliminary analysis of the measuring data supplied by a sensor connected to it. The base station 2 needs to have no own display facility since this function is assumed by the display device 4. Having a preliminary analysis in the base station 2 in combination with a final analysis in the display device 4 allows the volume of data to be transmitted to be kept low. Accordingly, the base station 2 needs just a small memory, a simple analytical unit, and little energy such that a patient is required to carry as little mass as possible on the body.

The display device 4 can be equipped with a large memory and complex analytical electronics, in particular a powerful microprocessor, and therefore can perform even extensive mathematical analyses of data over long periods of time. In particular, the display device 4 can test for a newly implanted sensor whether or not the new sensor works properly by means of a comparison with measuring data of earlier sensors or defined level and/or gradient values and form factors or samples. Moreover, the display device 4 allows its user the convenient entry of patient data, for example individual threshold values, whereby the display unit 4 can generate a warning signal when these are exceeded or not reached. In addition to an analytical, display, and warning function, the display device 4 can also assume the function of a data and communication center with regard to further components of the system, for example an injection device.

According to its purpose, the base station 2 and the sensor carrier unit 10 are carried on the body by a patient during the in-vivo measurements. In the process, the electrochemical sensor 3 projects into the body of the patient and is supplied by the potentiostat 48 that is contained in the base unit. While measuring, a current flows between the working electrode and the counter-electrode of the sensor 3 with its amplitude being correlated to the analyte concentration to be measured, such as being proportional to it in an ideal case. In the process, the potentiostat 48 varies the electrical potential applied to the counter-electrode such that the potential of the reference electrode of the sensor 3 remains constant.

The system 1 shown can be used to monitor an analyte concentration in the body of a patient in a continuous or quasi-continuous fashion. This means that the sensor 3 can be used to perform measurements in short time intervals of less than 5 minutes, in particular of less than 1 minute or even less than 10 seconds. A measurement can be effected in this context by means of digitizing a raw signal, for example an electrical current, in order to generate a measuring signal. Further data can be collected simultaneous with these measurements, for example temperature and/or electrode voltages that can be used for plausibility checking and/or error compensation.

Measurements are taken in the system 1 described here at time intervals of approx. one second, for example between 0.5 and 2 seconds, such that very large volumes of raw data accrue. The measuring signals supplied by the sensor 3 in time intervals of this type can be values of a continuous signal that has already been amplified and/or filtered, for example using a low-pass filter, in order to filter out electrical interference such as can be generated by the frequency of the public electrical power network (50 Hz or 60 Hz), noise or radio communication. The cut-off frequency of a low-pass filter of this type is preferably between 3 Hz and 50 Hz, in particular between 5 Hz and 20 Hz. In this context and in accordance with general usage, cut-off frequency is understood to mean the frequency at which the low-pass filter effects 3 dB of attenuation.

Low-frequency interference in the measuring signals that may arise, for example, from disturbances of the electrochemistry at interfaces between the sensor and surrounding body tissue, can be removed by means of filter algorithms, for example, by the repeated median procedure described in the application.

The measuring signals supplied by a sensor 3 being in operation are subjected to a preliminary analysis by the analytical unit 47 that is contained in the base station 2. In the process, the measuring signals are subjected to statistical analysis as raw data and condensed measuring data are thus produced from the raw data. The condensed measuring data are generated by the base station 2 for constant consecutive time intervals of, for example, one minute such that an unambiguous assignment of the time of the measuring data exists that results from the sequence and size of the time intervals. Subsequently, the condensed measuring data are transmitted in a wireless fashion to the display device 4 and further analyzed therein by means of an analytical unit, for example a microprocessor, in order to determine analyte concentration values.

In the exemplary embodiment shown, the base station 2 contains a memory in which the condensed measuring data can be stored such that they need not be transmitted right after being generated. The data sets stored can be provided with a check code that allows the condensed measuring data to be checked for data corruption and erroneous measuring data to be recognized in subsequent steps of analysis. Status information of the base station 2, for example the charge status of the battery, results of internal functional tests and similar information can also be stored in the memory jointly with the measuring data. This status information can be stored as status code, for example as byte, and taken into account in the analysis.

Particularly efficient storage of the condensed measuring data can be attained by storing only the deviation from a preceding measuring data value as the measuring data value. By this means, it is sufficient to fully store the first measuring data value in the memory. All subsequent values can then be characterized unambiguously by their difference from the preceding measuring data value such it is sufficient to store this difference.

The measuring signals to be condensed are stored only temporarily as raw data in the base station until the condensed measuring data are generated. The base station 2 therefore comprises a raw data memory whose content is overwritten as soon as a condensed measuring data value was determined for the measuring signals of a time interval and there is no longer a need for the measuring signals. It may be advantageous for some applications to provide for the option of later access to the raw data. This can be attained, for example, by transmitting raw data prior to over-writing them. This transmission can proceed unidirectional, i.e. without the reception of such data being confirmed by means of a receiving signal by a receiving device that stores the raw data. The base station 2 can comprise an additional transmitter for unidirectional transmissions.

Figure 2:
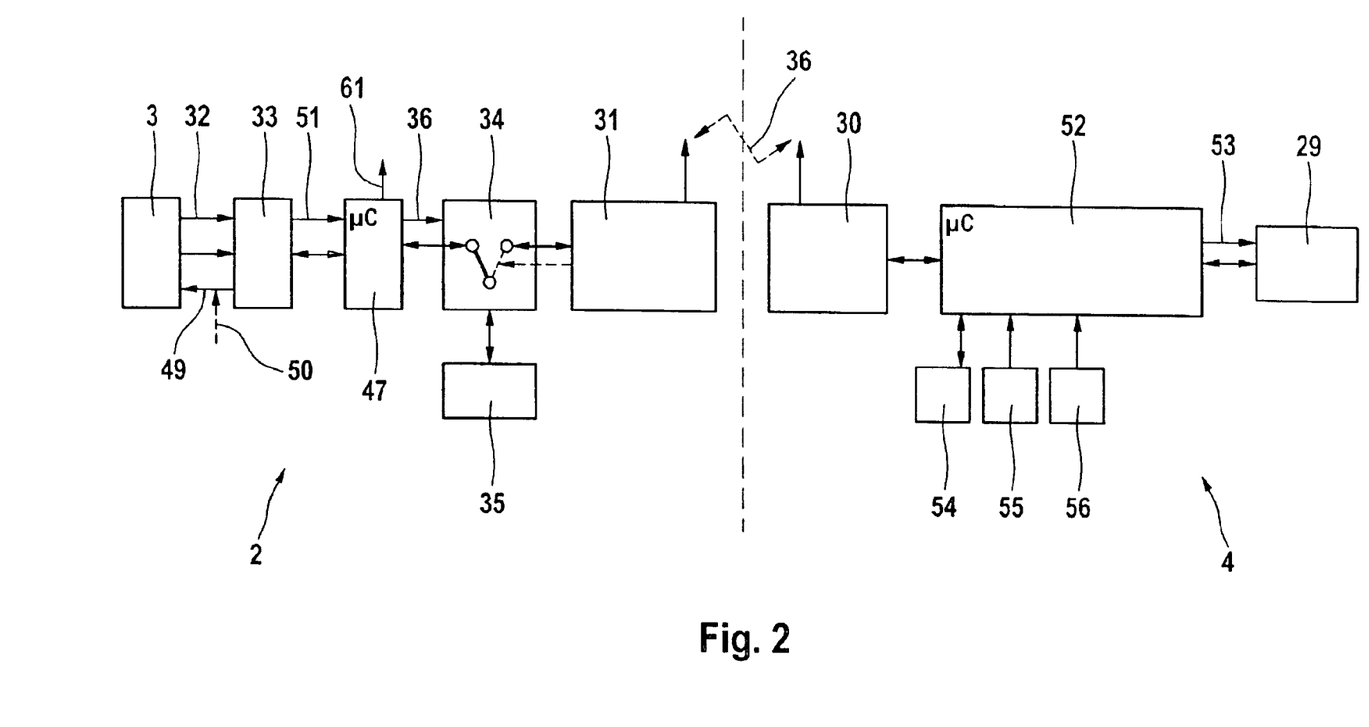
FIG. 2 shows a schematic view of the interaction of the system components of the exemplary embodiment shown in FIG. 1.

FIG. 2 shows a schematic view of the interaction of the various system components. To the left of the dashed line are shown the sensor 3 and components of a base station 2 connected thereto, whereas components of the display device 4 are shown to the right of the dashed line.

The base station 2, in operation, supplies the sensor 3 with voltage 49 of an amplitude that can depend on calibration data 50 that are stored on the data carrier 11 shown in FIG. 1. The sensor 3 supplies measuring signals 32 that are being digitized by an analog-digital converter 33 and subsequently subjected to statistical analysis as digital raw data 51 by the analytical unit 47, preferably a microprocessor. In the process, condensed measuring data 36 are generated from the raw data 51. The condensed measuring data 36 are placed in a memory 35 that can be accessed both by the analytical unit 47 and the communication unit 31 that contains a transmitter and a receiver. In order to prevent access conflicts, the analytical unit 47 and the communication unit 31 are connected to the memory 35 by means of a changeover switch 34 which provides access to the memory 35 either to the analytical unit 47 or to the communication unit 31 depending on its switch status.

The communication unit 31 of the base station 2 reads-out the condensed measuring data 36 from the memory 35 and transmits them to a communication unit 30 of the display device 4. In the exemplary embodiment shown, the communication unit 30 contains a transmitter and a receiver such that a bidirectional data exchange is feasible. However, it is also feasible for the condensed measuring data 36 to be transmitted unidirectionally by the communication unit 31 of the base station 2. It is feasible, in particular, to equip the analytical unit 47 with a transmitter 61 for unidirectional transmission of raw data.

The condensed measuring data 36 are analyzed in the analytical device 4 by the analytical unit 52, for example a microprocessor, contained therein in order to determine analyte concentration values 53 that can be displayed by the display facility 29 and stored in a memory 54, like the condensed measuring data 36. During the analysis of the condensed measuring data 36, the analytical unit 52 of the display device 4 also performs a calibration taking into account measuring results of a measuring device 56 that is integrated into the display device 4 and determines the analyte concentration of a body fluid sample that was obtained, for example, from a small puncturing wound.

During the analysis of the condensed measuring data 36, the analytical unit 52 of the display device 4 can add a time of day and a date to the condensed measuring data 36 and the analyte concentration values determined therefrom by using a real-time clock 55, since the condensed measuring data apply to time intervals of constant duration.

The statistical analysis of the measuring signals in the base station 2 can, in the simplest of cases, be the formation of a mean. However, the statistical analysis can just as well include filter and/or correction algorithms to exclude or correct error-containing values from the further analysis by filtering. Kalman filter procedures, for example, are suitable for this purpose.

A repeated median procedure can be used as method for filtering and condensing of the raw data. In a procedure of this type, the median value of the slopes between pairs of measuring signal values of a time interval is formed. Extreme, and therefore implausible, raw data values can be disregarded in this formation of the median, for example values that deviate by more than a given threshold value from the mean of all remaining raw data values of said time interval. However, it is also feasible in the formation of the median to actually take into account in the formation of the median of the slope all pairs of values that can possibly be formed from the raw data values of said time interval.

A measuring data value is then calculated for the current time interval from the median value of the slope and the condensed measuring data value for the preceding time interval. For this purpose, the product of the median value of the slope times the duration of the time interval can be added to the measuring data value of the preceding time interval. For the very first time interval, the median, for example, of the raw data values contained in said time interval can be used as condensed measuring data value.

In the repeated median procedure described above, it is favorable to select the time intervals for which a condensed measuring data value each is calculated from the median of the slope and the preceding measuring data value such that they overlap. It is also feasible, in particular, to apply the repeated median procedure multiply, i.e. to generate, for example, condensed or compressed measuring data values from raw data values in a first step and to further compress the compressed measuring data values by repeated application of the repeated median procedure in a further step.

To have a two-stage analysis, in which a first stage of analysis is performed in the base station 2 and a second stage of analysis is performed in the display device 4, allows even very large volumes of raw data to be processed and thus to fully reap the advantages of continuous or quasi-continuous measurement with regard to relatedness to real-time and accuracy. Despite this fact, only small data volumes need to be transmitted from the base station 2 to the display device 4. Consequently, the energy consumption of the base part 2, which is being carried on the body, is low such that a small, light-weight, and cost-efficient battery 5 is sufficient to satisfy the energy need of the base part 2 and sensor carrier unit 10. The two-stage analytical procedure therefore contributes to reducing, to the extent possible, the weight the patient needs to carry on the body and thereby increasing the user convenience.

In order to minimize the data traffic between the base station 2 and the display device 4, a complete analysis of the raw data could be effected in the base station 2 such that only analyte concentration values needed to be transmitted to the display device 4. In the two-stage analysis described above, though, only little processor power is required in the base station 2 such that a particularly cost-efficient microprocessor can be used as analytical unit 47. It is another advantage of the two-stage analytical procedure described above that a calibration of the measuring data can be performed in the display device 4 within the scope of the second analytical step by means of a control measurement. For this purpose, the display device 4 contains a measuring facility for determining an analyte concentration of a body fluid sample. This measuring facility can, for example, be structured in accordance with commercial blood sugar measuring devices and determine the glucose concentration of a body fluid sample that is applied to a test strip 28 by photometric or electrochemical means. Since the analytical unit of the display device 4 is connected to the measuring facility, the analyte concentration values that have been determined on body fluid samples can be used for calibration during the analysis of measuring data that have been transmitted to the base station 2.

Aside from a measuring facility for determining an analyte concentration of a body fluid sample, the display device 4 can also comprise an input option for the input of patient data. Patient data can be, for example, information regarding meals that have been taken up or individual threshold values for the measuring data, with a warning signal being generated when these are exceeded or not reached. Moreover, the display device 4 can be adapted for communication with additional system components, for example an injection device or a higher-level HOST system, for example the PC of a physician, care provider or clinic.

The display device 4 is equipped with a transmitter 30 for transmitting control signals and the base station 2 is equipped with a receiver 31 for receiving control signals as well as with an electronic memory for storing the condensed measuring data. The transmission of the condensed measuring data is triggered by a control signal that is transmitted by the display device 4. The display device 4 confirms receipt of the measuring data by transmitting a confirmation signal.

The display device 4 contains a clock for determining the actual time. When the display device 4 receives condensed measuring data from the base station 2, the current measuring data value can be marked with a current time mark, in which the current time of day and date are coded, and stored. The time marks of forward-progressive measuring data values can be calculated based on said time mark. If, for example, a condensed measuring data value is generated for consecutive time intervals of one minute each, the time of day for which measuring data values were determined can be calculated for all measuring data values by incrementally decreasing the time by one minute each.

The display device 4 contains a memory that is sufficiently large to store measuring data that were determined over multiple sensor carrying periods, i.e. over multiple days using different sensor carrier units 10. In the process, measuring data from different sensors 3 can each be provided with a sensor identifier such that information, such as the measuring time, can be calculated for the individual measuring data values from the sensor identifier and the time of day the measuring data of a sensor were received.

Upon repeated access of the display device 4 to the base station 2 in the exemplary embodiment shown, only measuring data that have been newly generated in the meantime are transmitted in order to minimize the transmission time and transmission energy. The time of the most recent access can be stored in the display device 4 in a data header, in which other general data, for example identifiers of the sensor carrier unit and time format, e.g. Universal Time Convention, can be stored as well.

The memory of the base station 2, in which the condensed measuring data are stored, can be provided with a lock that permits over-writing of measuring data when a new sensor carrier unit 10 is connected only after the measuring data have been sent to the display device 4 and receipt of the data has been confirmed. For example, the start-up of the base station 2 that is effected by connecting a new sensor carrier unit 10 may initially effect the transmission of existing measuring data before new measuring data are recorded However, it is also feasible to select the memory of the base station 2 to be sufficiently large such that more measuring data than those generated with one sensor carrier unit 10 in, for example, 5 days can be stored in the memory of the base station 2 before it needs to be replaced. Automatic transmission of measuring data prior to replacement of a sensor carrier unit 10 can ensure that a time mark can be determined by the display device 4 for all measuring data that are stored in the base station 2. Unless measuring data are generated continuously, there is a risk of data loss with regard to the allocation to an unambiguous time mark.

During replacement of a sensor it is common that no measuring data are generated for an indefinite period of time. In order to ensure that each measuring value can be allocated unambiguously to an absolute time, a sensor start data and time of day is stored for each sensor in the memory of the base station 2. If transmission of any old data, generated using the preceding sensor, to the display device 4 is required prior to the connection of a new sensor, the sensor start date and time of day can be made available without any difficulty by the display device 4. The sensor start date can be stored in the base station 2 and can be stored in a data header that is transmitted jointly with condensed measuring data. However, it is also feasible to store the sensor start-up date and time of day in the display device and utilize it to determine the times of the individual measuring data values. If measuring values for constant consecutive time intervals are determined, this allows to determine for each measuring value at which time it was measured even upon a change of sensors.

FIG. 1 shows connection contacts 6a, 6b, 6c of the base station 2 for connecting the sensor 3, and connection contacts 7a, 7b of the base station 2 for connecting the battery 5. Moreover, the base station 2 further has at least one data input 8a, 8b for connection and read-out of a data carrier 11 bearing calibration data. These calibration data identify the sensitivity of the sensor 3, which is an electrochemical sensor that contains, for example, an enzyme that generates, by catalytic conversion of the analyte, charge carriers that can be measured in the form of an electric current flowing between the electrodes of the sensor. If the analyte is glucose, for example, the enzyme can be a glucose oxidase.

Usually, sensors for measuring analyte concentrations of body fluids, for example blood or interstitial fluid, cannot be manufactured to have exactly predetermined measuring sensitivities. Typically, there is substantial variation of the sensor sensitivity between production batches that can be taken into account in the analysis of measuring signals of a sensor by means of calibration data. The calibration data usually are determined by the manufacturer either using the respective sensor itself or by means of random samples of other sensors of the respective production batch. Calibration data of this type generally describe the difference between an ideal sensor sensitivity and a determined sensor sensitivity.

The data input 8a, 8b is coupled to spring elements 9 that render connecting a data carrier easier by means of spring force. Preferably, the data carrier 11 is a memory chip such that the data input is formed by electrical connection contacts. The data carrier 11 can, for example, just as well be an RFID or a magnetic data carrier, and, accordingly, the data input 8a, 8b can comprise a reading head. In the exemplary embodiment described, the calibration data that are read by the data carrier 11 are transmitted from the base station 2 to the display device 4 and used therein for analysis of the measuring data. It is also feasible to already process the calibration data in the base station 2 and generate condensed measuring data, in which the calibration data are taken into account. This allows a risky mix-up of data carriers 11 bearing calibration data for different sensors 3 by a user to be prevented.

The base station 2 contains a test circuit 26 that is connected to the potentiostat 48 and supplies one response signal or more response signals to the analytical unit 47 of the base station 2 during a system test, which response signal(s) is/are analyzed by the analytical unit 47, whereby the analytical unit 47 compares a value of the at least one response signal to an expected value and generates an error signal if the value of the at least one response signal deviates from the expected value by more than a predetermined tolerance value. This error signal can be transmitted, for example, via the transmitter 31 to the display device 4 which, in turn, indicates the error to a user. The test circuit simulates a sensor 3 being connected to the potentiostat 48 such that the analytical unit 47 can use the test circuit 26 to check the proper function of the potentiostat 48 and the charging status of the battery 5. In the simplest case, the test circuit 26 can be provided in the form of a switchable fixed-value resistor.

The housing 12 of the sensor carrier unit 10 has at least two separate chambers 13, 14, 15, whereby the sensor 3 is disposed in the first chamber 13 under sterile conditions, and the data carrier 11 bearing calibration data of the sensor 3 and a battery, if applicable, are disposed in a second chamber 14. In the exemplary embodiment shown, the battery 5 is disposed in a third chamber 15.

The housing 12 is adapted to an interface of the base station 2 such that the sensor 3 contained in the housing 12 and the corresponding data carrier 11 can be connected to the base station 2 by placing the housing 12 against the interface. Connecting the sensor carrier unit 10 to the base station 2 initializes the measuring system 1 automatically and starts-up the measuring process.

The housing 12 contains a spring element 20 that supports the process of connecting the battery 5 when the housing 12 is placed against the interface of the base station 2. In corresponding fashion, spring elements can be disposed also in the first chamber 13 and in the second chamber 14 in order to support the process of connecting the sensor 3 and/or the data carrier 11 to the base station.

In the exemplary embodiment shown, the housing 12 and the interface of the base station 2 are adapted to each other such that, firstly, the battery 5 and the data carrier 11 are connected to the base station 2 when the housing 12 is placed against the interface, and only thereafter the sensor 3 gets connected to the base station 2 by means of the contacts 6a, 6h, 6c that are provided for this purpose. In the exemplary embodiment shown, the sensor 3 is flat in structure and is connected to the base station 2 by means of a zero insertion force connector 3a. The sensor 3 can just as well be of sandwich structure or made up to be wire-shaped or rotationally symmetrical and the contacts 6a, 6b, 6c may be provided to match.

In this context, a seal 21 of the base station 2, which is provided in the form of a gasket in the exemplary embodiment shown, provides for water-tight coupling of the sensor 3 to the base station 2, such that no moisture can penetrate into the internal space of the base station 2. Accordingly, the base station 2 can be carried, for example, on the stomach of a patient without getting damaged by body fluids. The seal 21 effects high-resistance sealing of the base station 2 and the connected sensor 3. By this means, the sensor 3, being provided in the form of an electrochemical sensor, can be supplied with voltage by means of the potentiostat 48 that is disposed in the base station 2 without any interference by leakage currents.

Figures 4, 5:
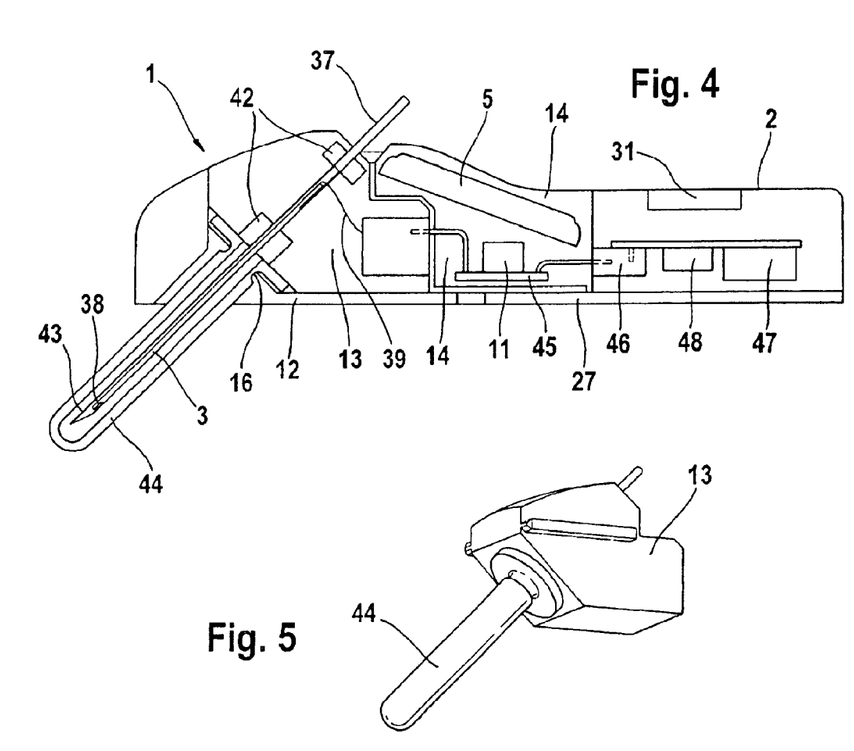
FIG. 4 shows a cross-sectional view related to FIG. 3.
FIG. 5 shows a sensor housing of the exemplary embodiment shown in FIGS. 3 and 4.

FIG. 3 shows an oblique view of an exemplary embodiment of the base station 2 with sensor carrier unit 10 being connected to it. FIG. 4 shows a cross-sectional view related to FIG. 3, in which the sterile housing chamber 13 and sensor 3 disposed therein as well as the second housing chamber 14 and battery 5 and data carrier 11 of the sensor carrier unit 10 being disposed therein are shown. Also shown is that the base station 2 contains a potentiostat 48 for supplying current and voltage to the sensor 3, and an analytical unit 47 that is provided in the form of a microprocessor, and a transmitter and a receiver 31 for wireless communication with the display device 4, whereby the antenna or antennae for wireless communication with the display device 4 are surrounded by the housing of the base station 2.

Like the housing of the base station 2, the housing 12 of the sensor carrier unit 10 is made of rigid plastic material. The interfaces of base station 2 and sensor carrier unit 10 are provided for a form-fitting connection in the exemplary embodiment shown. The housing 12 comprises catch pegs 40 that engage recesses of the base station 2 that match them. These recesses are disposed on the outsides of two spring legs 41 such that the catch pegs are pressed into the recesses by spring force. The spring legs 41 can be compressed such that the catch pegs 40 of the sensor carrier unit 10 detach from the recesses matching them and the sensor carrier unit 10 can be taken off the base station 2. With the spring legs 41 being compressed, the sensor carrier unit 10 can be placed against the base station 2 in corresponding fashion.

Alternatively or in addition to a form-fitting connection, the sensor carrier unit 10 can just as well be provided such that it can be connected to the base station 2 in a friction-locked fashion.

The cross-sectional view shown in FIG. 4 shows that the sensor carrier unit 10 comprises two separate chambers 13, 14, whereby the sensor 3 is disposed in a first chamber 13 under sterile conditions and a data carrier 11 bearing calibration data of the sensor 3 and a battery 5 for supplying electrical power to the base station 2 are disposed in the second chamber 14. Connection lines of the sensor 3 lead out from the first chamber 13 into the second chamber 14 to a printed board 45 that is contacted to the data carrier 11 that is provided in the form of a memory chip. The printed board 45 is connected to the base station 2 by means of a plug-in connection 46, a multi-pole plug-in connection in the exemplary embodiment shown.

The sterile chamber 13, in which the sensor 3 is stored, is closed off by means of two Septa 42, whereby an insertion needle 43 for insertion of the sensor 3 into a human or animal body is guided through the Septa 42. The front end of the insertion needle 43 protruding from the housing chamber 13 is surrounded by a sterile protective cap 44 that is taken off only when the sensor 3 is to be inserted into a human or animal body by means of the insertion needle 43. The sterile protective cap 44 envelopes the insertion needle without touching it and is connected to the remaining housing 12 by a predetermined breakage site 16.

For carrying convenience, it is advantageous for the sensor carrier unit 10 to have a sensor opening through which the sensor 3 or its connection line 39 is guided and which is situated as far as possible from the edge of the bottom 27 of the sensor carrier unit 10 in order to minimize tilting moments. In the exemplary embodiment shown, the sensor opening is disposed to be situated more than 1 cm distant from the edge of the bottom 27. It is feasible just as well, in particular, to dispose the sensor opening in the center of base plate 27, or in a position that deviates from the center by less than 20% of the length of the base plate, in particular deviates from the center by less than 10% of the length of the base plate.

For insertion of the sensor 3, the sensor carrier unit 10 is disposed, fur example, on the stomach of a patient and the insertion needle 43 is punctured into the body of the patient. Subsequently, the insertion needle 43, which can, for example, be provided in the form of a groove carrying the sensor 3, can be retracted from the body of the patient, whereby the sensor 3 remains inside the body of the patient. In order to attain particularly good sealing against pathogens, a front region, in the direction of puncturing, of the insertion needle 43 can be provided in the form of an open groove adjacent to which there is a region that is provided in the form of a tube. Said tube-shaped region can be guided through a septum closing off the housing such as to be sealed against pathogens.

As a matter of principle, the insertion can proceed under any angle between the direction of puncturing and the surface of the skin. Angles between 30° and 60° are particularly advantageous for an insertion into subcutaneous fatty tissue. The sensor 3 has a sensor head 38 that is designed to be implanted and an electric connection line 39 that is connected to the sensor head 38, whereby the connection line is guided in an arc in the housing 12 of the sensor carrier unit 10, preferably being arced by 30° to 150°. The sensor carrier unit 10 shown is provided such that a user can actually see the puncturing site during the insertion of the sensor 3.

The sensor carrier unit 10 has a base plate 27 which, according to its purpose, is glued to the body of the patient. The base station 2 is placed on the sensor carrier unit 10, on the base plate 27 to be more exact. The housing of the base station 2 then touches laterally against the housing 12 of the sensor carrier unit 10. The base plate 27 has an adhesive surface that is protected by a film that can be peeled off, and which is multi-part and whose parts each cover different areas of the adhesive surface and are separated from each other when the film is peeled off. Said adhesive surface can, for example, be provided in the form of a double-sided adhesive film or a pad that is adhesive on both sides such that one adhesive surface can be glued to the bottom side of the sensor carrier unit 10 and the other adhesive surfaces, according to its purpose, can be glued to the skin of a patient. The films for protecting the adhesive surfaces can be provided like in commercial plasters. The films can be removed more easily from the adhesive surfaces if the adhesive surfaces are protected by multi-part films. By this means it is possible, for example, to proceed with adhesively attaching the sensor carrier unit 10 only after insertion of the sensor, since the individual parts of the films protecting the adhesive surfaces can be pulled from under the sensor carrier unit 10 from different directions.

Preferably, the carrier of the adhesive surface, for example a film or a pad, is stretchable such that the carrier can be removed from the body of the patient at a later time by pulling with the force vector of pull extending parallel to the plane of the adhesive surface. Adhesive pads with corresponding elastic properties are commercially available, for example for attaching posters, under the brand name of tesa powerstrips.

A carrier of the adhesive surface that is suitable for attaching the sensor carrier unit 10 can be made, for example, from a foam, in particular a polyurethane foam. A carrier made of foam has the additional advantage that it reduces relative motions of the body with respect to the sensor carrier unit 10.

During the manufacture of the sensor carrier unit 10, the sensor 3 is initially disposed in the first housing chamber 13 and the chamber is then sealed. In order to manufacture the exemplary embodiment shown in FIG. 4, a sterile protective cap 44 is also disposed in this assembly step around the end of the sensor 3 that protrudes from the first housing chamber 13 and around the insertion needle 43 that carries the sensor 3, and the sterile protective cap 44 is connected to the housing chamber 13. Subsequently, the housing chamber 13 is exposed to intense radiation, for example electron radiation, such that the sensor 3 and the insertion needle 43 are sterilized. FIG. 4 shows a detailed view of the first housing chamber 13 with the sterile protective cap 44 being attached to it and these being sterilized jointly by radiation exposure after insertion of the sensor 3.

In a further assembly step, the first housing chamber 13 is joined with the second housing chamber 14 in order to create the sensor carrier unit 10. In this process, an insertion aid 37 can be attached to the sensor carrier unit 10 that renders the puncturing of the sensor 3 and/or of an insertion cannula carrying the sensor into the body of a patient easier. The insertion aid can comprise a spring that can already be pre-tensioned on delivery of the sensor carrier unit or can be tensioned by the user by means of a pre-tensioning lever (not shown). A user can trigger the tensioned insertion spring by actuating a trigger button and thus effect a puncturing of the sensor or of an insertion cannula 43 carrying it.

In the exemplary embodiment described previously, the sensor carrier unit 10 communicates with the base station 2 via electrical lines. The sensor carrier unit 10 therefore has an interface having electrical contacts 3a, 3b, 3c that contact electrical contacts 6a, 6b, 6c of an interface of the base station 2 in order to couple the sensor carrier unit 10 to the base station 2. However, the exemplary embodiment described previously can just as well be modified such that the sensor carrier unit 10 communicates with the base station 2 in a wireless fashion. A data exchange can proceed, for example, by inductive coupling or RFID. This means makes the sealing of the base station 2 and also of the sensor carrier unit 10 easier. As another advantage of this measure, the risk of falsification of measuring signals by leakage currents can be reduced markedly.

A sensor carrier unit 10 that is equipped for wireless communication with a base station 2 contains a potentiostat 48, like the one disposed in the base station 2 in the exemplary embodiment described previously. The sensor carrier unit 10 preferably contains, in addition, a pre-amplifier for amplification of sensor signals.

The advantages of supplying power to the base station 2 by means of a battery 5 that is disposed in the sensor carrier unit 10 can be utilized also in the case of a wireless communication between the sensor carrier unit 10 and the base station 2. For example, energy can be transferred from the sensor carrier unit 10 to base station 2 via inductive coupling. In order to generate the alternating voltage required for inductive coupling, a chopper can be disposed in the sensor carrier unit 10 in addition to the battery 5.

Figure 6:
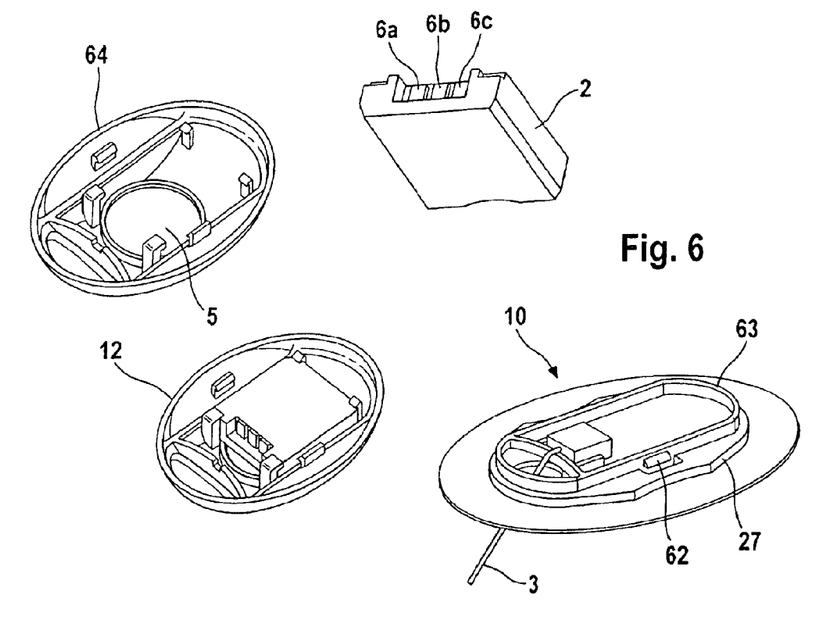
FIG. 6 shows components of a further exemplary embodiment.

FIG. 6 shows components of a further exemplary embodiment that differs from the exemplary embodiment described previously only in its mechanical structure. The base station 2 is structured in the form of an electronics unit that has contacts 6a, 6b, 6c for connection to a sensor 3 and, like the base station 2 of the exemplary embodiments described previously, contains an analytical unit, a potentiostat, a test circuit as well as transmitter and receiver for communication with a display device. Unlike the exemplary embodiments described previously, the base station 2, in use, is protected by a removable housing that is formed by a base plate 27 and a housing lid 64 that can be placed thereupon.

In order to protect its electronic components while it is being handled by the user, the base station 2 has a separate housing which preferably is not removable. This housing can also effect electrical screening and insulation. It can, for example, be made of an epoxy casting compound or of injection molding parts.

The base plate 27 that is carried on the body forms the sensor carrier unit 10 in the exemplary embodiment shown in FIG. 6. The base plate 27 has a hole through which the sensor 3 can be inserted into body tissue of a patient during the insertion process. According to purpose, the housing lid 64 is placed on the base plate 27. The base plate 27 has catch or locking elements in order to hold the housing lid 64 in place. In addition, the base plate 27 carries a seal 63, for example an O-ring or a sealing lip, for sealing an internal space that is then enveloped by the base plate 27 and the housing lid 64. Seal 63 and catch means can, alternatively or in addition, be provided just as well on the housing lid 64.

Figure 7:
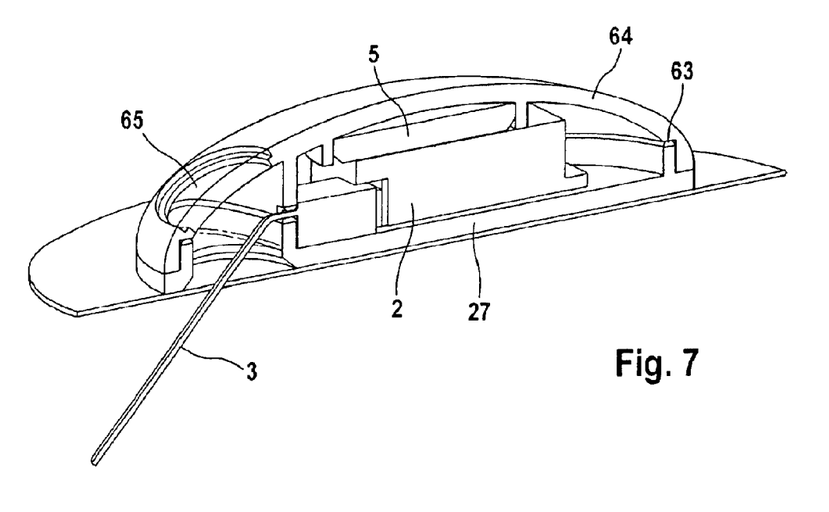
FIG. 7 shows a longitudinal sectional view of the components shown in FIG. 6 in the assembled state.

FIG. 7 shows a longitudinal sectional view through the system components, in the assembled state, shown in FIG. 6, in which a patient carries the unit on the body. In the process, the seal 63 effects sealing at the sensor shaft in front of the contacts 6a, 6b, 6c of the base station 2 such that these are protected in a hermetically sealed internal space.

The housing lid 64 has a transparent viewing window 65 through which the sensor puncturing site and thus the hole provided in the base plate 27 for the sensor 3 can be viewed.

Having this viewing window 65 thus allows the sensor puncturing site to be checked visually such that problems, for example inflammations, can be detected at an early time.

FIG. 6 shows that a battery 5 is disposed in the housing lid 64. However, the battery 5 can be disposed in the base plate 27 just as well. It is preferred for the battery 5 to be easy to remove by the user after removal of the housing lid 64 such that the battery can be disposed of separately.

Base plate 27, housing lid 64, battery 5, and sensor 3 are consumables designed for single use only, whereas the base station 2 can be used multiply. The consumable parts are packaged jointly with an injection aid 66 shown in FIGS. 8 to 10 during the manufacturing process and sterilized by exposure to radiation. Sterilization of the battery 5 is not absolutely necessary.

Figure 8:
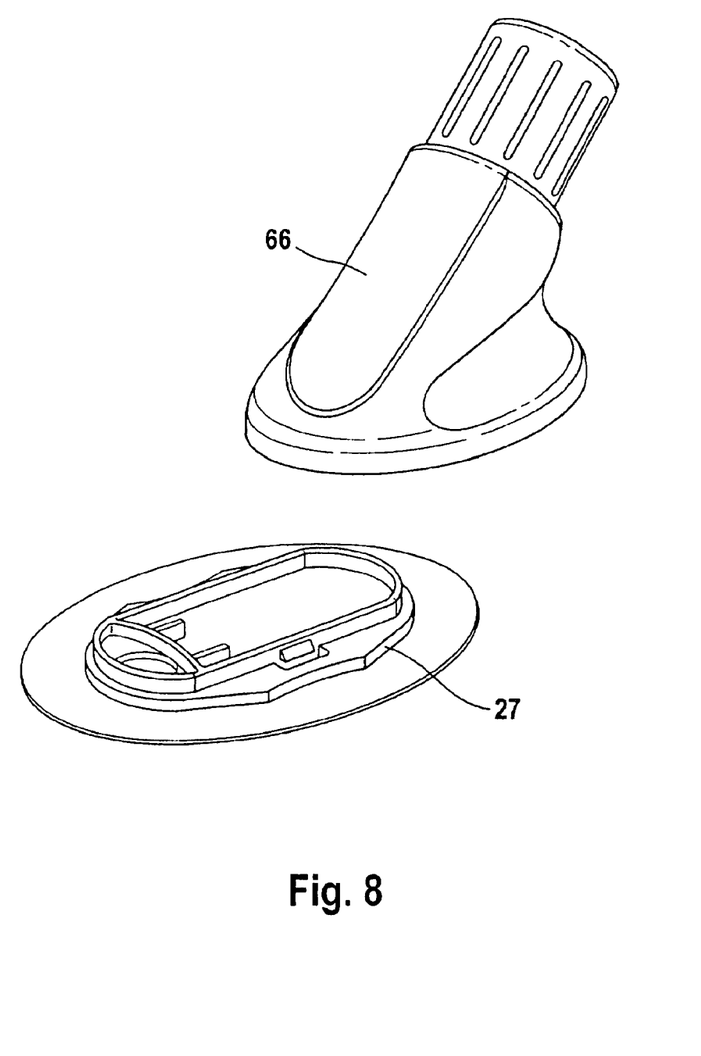
FIG. 8 shows a base plate of the exemplary embodiment shown in FIG. 7 having an insertion aid for application of the sensor in the body of a patient.
Figure 9:
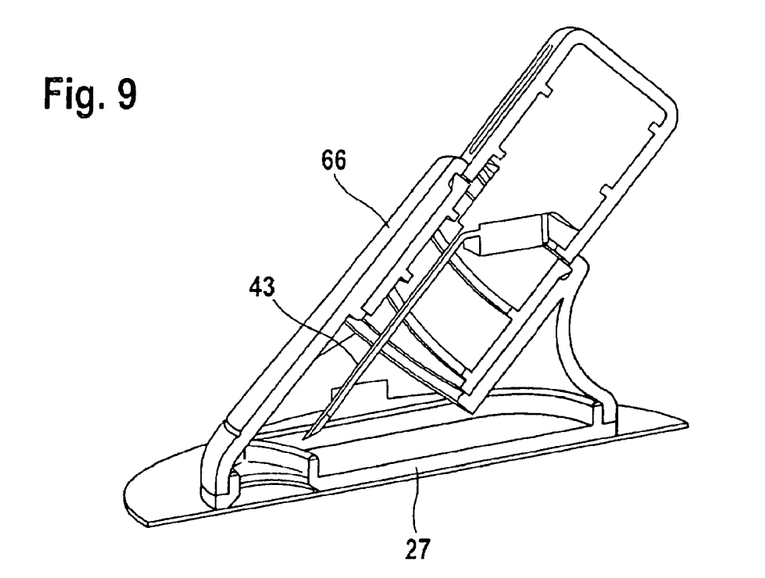
FIG. 9 shows a longitudinal sectional view through the base plate shown in FIG. 8 having the insertion aid placed on it, before application of the sensor; and, FIG. 10 shows a longitudinal sectional view through the base plate shown in FIG. 8 having the insertion aid placed on it, after application of the sensor.
Figure 10:
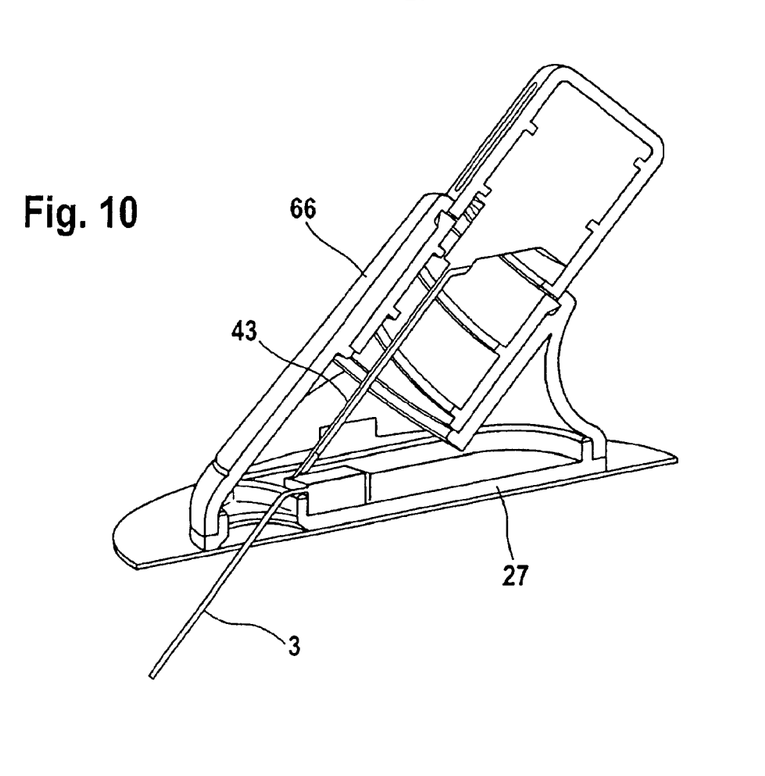

FIGS. 8 to 10 illustrate the individual steps involved in the application of a sensor 3 in the body of a patient. In a first step, the base plate 27 is glued to the body of a patient. Then an insertion aid 66 is placed on the base plate 27, the insertion aid 66 preferably catches onto the base plate 27. FIG. 9 shows a longitudinal sectional view of the insertion aid 66 with a matching base plate 27. The insertion aid 66 contains an injection needle 43 that can be punctured through the opening of the base plate 27 into the body of a patient. In the process, a sensor 3 that has been disposed in the injection needle 43 by its manufacturer, is inserted into the body of a patient.

The sensor 3 is advanced jointly with the insertion needle 43 by the user in a guided linear motion at an angle that is predetermined by the insertion aid 66. This linear motion can just as well be effected by rotation or a shear motion though this should best not generate a transverse motion with respect to the puncturing site. The insertion motion can also be effected with an automatic mechanism. For example, the puncturing of the insertion needle 43 can be supported by a spring.

After the puncture, the insertion needle 43 is retracted, whereby the sensor 3 remains inside the body of the patient. Subsequently, the insertion aid 66 can be removed from the base plate 27. In a final step, the housing lid 64 having a base station 2 contacting the battery 5 disposed therein is placed on the base plate 27. The base station 2 thus contacts the sensor 3. The system then commences to work automatically. Accordingly, as soon as the housing lid 64 having a base station 2 is placed on the base plate 27, measuring signals are generated and subjected to statistical analysis and condensed by the analytical unit contained in the base station 2. The condensed raw data generated by this means are transmitted by a transmitter of the base station 2 to a display device 4, as is shown in FIG. 1.

Preferably, a data carrier 11 (not shown) bearing calibration data of the sensor 3 is situated on the housing lid 64 or on the base plate 27, as is described with reference being made to FIG. 1, which data carrier II contacts the base station 2 and is read-out by it in the operational state shown in FIG. 7.

Thus, embodiments of the system for in-vitro measurement of an analyte concentration are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A method of compressing data from in-vivo measurement of an analyte concentration in a human, comprising:
providing a sensor configured for in-vivo measurement of the analyte concentration;
providing a base station having a processor configured to execute instructions for processing signals of the measurement sensor and a memory operably coupled to the processor;
forming, by the processor, pairs of measurement signals from raw data values of in-vivo measurements of the analyte concentration generated for a first time interval;
determining, by the processor, a slope of a line connecting each pair of measurement signals;
calculating, by the processor, a median value of each slope of the line connecting each pair of measurement signals;
calculating, by the processor, a compressed data value for the first time interval from the median value of each slope of the line connecting each pair of measurement signals and a compressed data value of a preceding time interval;
providing, by the processor, a plurality of raw data values for a later time interval;
forming, by the processor, pairs of measurement signals from the raw data values for the later time interval; and
calculating, by the processor, a compressed data value for the later time interval from the compressed data value of the first time interval and a slope value of a line connecting each pair of measurement signals determined for the later time interval.

2. The method as in claim 1, further comprising, disregarding, by the processor, raw data that are a substantial deviation from other raw data values.

3. The method as in claim 1, further comprising, determining, by the processor, raw data values consecutively over constant time intervals using time marks including a date and a time.

4. The method as in claim 1, wherein, calculating a median value includes disregarding, by the processor, raw data values that deviate by more than a threshold value from a mean value of other raw data values.

5. The method as in claim 1, further comprising, sending, by a transmitter of the base unit, the calculated compressed data value from a base station to a display device.

6. A method of compressing data from in-vivo measurement of an analyte concentration in a human, comprising:
providing a sensor configured for in-vivo measurement of the analyte concentration;
providing a base station having a processor configured to execute instructions for processing signals of the measurement sensor and a memory operably coupled to the processor;
providing, by the processor, a plurality of consecutive raw data values of in-vivo measurements of the analyte concentration for a first time interval;
calculating, by the processor, a compressed data value for the first time interval by calculating a median value of a slope of a line connecting the consecutive raw data values for the first time interval and a compressed data value of a preceding time interval;
providing, by the processor, a plurality of raw data values for a later time interval; and
calculating, by the processor, a compressed data value for the later time interval from the compressed data value of the first time interval and a slope value of a line connecting the raw data values determined for the later time interval.

7. The method as in claim 6, wherein the later time interval overlaps the first time interval.

8. The method as in claim 6, wherein, calculating, by the processor, a median value of the raw data values includes disregarding raw data values that deviate by more than a threshold value from a mean value of other raw data values.

9. The method as in claim 6, further comprising, sending, by a transmitter of the base unit, the calculated compressed data value for the later time interval from a base station to a display device.

10. A method of compressing data from in-vivo measurement of an analyte concentration in a human, comprising:
providing a sensor configured for in-vivo measurement of the analyte concentration;
providing a base station having a processor configured to execute instructions for processing signals of the measurement sensor and a memory operably coupled to the processor;
forming, by the processor, pairs of raw data values of in-vivo measurements of an analyte concentration, which were generated for a first time interval;
determining, by the processor, for each pair of raw data values, a slope value of a line connecting the pair of raw data values;
calculating, by the processor, a median value of the slope values of lines connecting the pairs of raw data values;
calculating, by the processor, a compressed data value for the first time interval from the median slope value and a compressed data value of a first preceding time interval;
forming, by the processor, pairs of compressed data values generated for a second time interval containing a plurality of first time intervals, the second time interval being at least ten times longer than the first time intervals;
determining, by the processor, for each pair of compressed data values, a slope value of a line connecting the pair of compressed data values;
calculating, by the processor, a median value of the slope values of lines connecting pairs of compressed data values; and
calculating, by the processor, a condensed data value for the second time interval from the median value of the slope values of the lines connecting pairs of compressed data values and a condensed data value of a second preceding time interval.

11. The method of claim 10, wherein the second time interval overlaps the second preceding time interval.

12. The method as in claim 10, wherein, calculating a median value of the slope values of lines connecting the pairs of raw data values includes disregarding, by the processor, raw data values that deviate by more than a threshold value from a mean value of other raw data values.

13. The method as in claim 10, further comprising, sending, by a transmitter of the base unit, the condensed data value for the second time interval from a base station to a display device.

14. The method as in claim 1, wherein the later time interval is at least ten times longer than the first time interval.

15. The method as in claim 6, wherein the later time interval is at least ten times longer than the first time interval.

* * * * *

UNITED STATES PATENT AND TRADEMARK OFFICE
CERTIFICATE OF CORRECTION

| | |
|---|---|
| PATENT NO. | : 9,636,049 B2 |
| APPLICATION NO. | : 14/076428 |
| DATED | : May 2, 2017 |
| INVENTOR(S) | : Bernd Roesicke et al. |

It is certified that error appears in the above-identified patent and that said Letters Patent is hereby corrected as shown below:

On the Title Page

Item (73), "ROCHE DIAGNOSTICS OPERATIONS, INC." should read --ROCHE DIABETES CARE, INC.--

Signed and Sealed this
Thirtieth Day of May, 2023

Katherine Kelly Vidal
*Director of the United States Patent and Trademark Office*